United States Patent [19]

Oiry et al.

[11] 4,314,076

[45] Feb. 2, 1982

[54] CYSTAMINE DERIVATIVES SUITABLE FOR USE AS MEDICAMENTS

[75] Inventors: Joël Oiry; Jean-Louis Imbach, both of Montpellier, France

[73] Assignee: Agence Nationale de Valorisation de la Recherche (ANVAR), Neuilly s., Seine, France

[21] Appl. No.: 160,183

[22] Filed: Jun. 17, 1980

[30] Foreign Application Priority Data

Jun. 19, 1979 [FR] France .................................. 79 15672

[51] Int. Cl.$^3$ ...................... C07C 127/15; A61K 31/17
[52] U.S. Cl. ........................................ 564/33; 424/322
[58] Field of Search ............................ 564/33; 424/322

[56] References Cited

FOREIGN PATENT DOCUMENTS 4035252  9/1974  Japan ..................................... 564/33

OTHER PUBLICATIONS

Kortselius, CA 89:190810x (1978).

*Primary Examiner*—Thomas A. Waltz
*Attorney, Agent, or Firm*—Weiser, Stapler & Spivak

[57] ABSTRACT

The invention relates to new chemical compounds.

The compounds according to the invention are compounds of the following formula

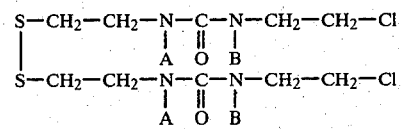

in which one of the substituents A and B is hydrogen and the other is the radical —N=O.

These compounds are suitable for use as medicaments.

2 Claims, 7 Drawing Figures

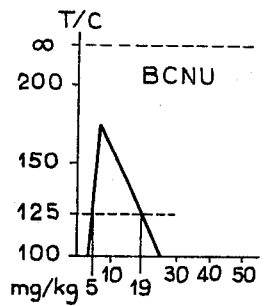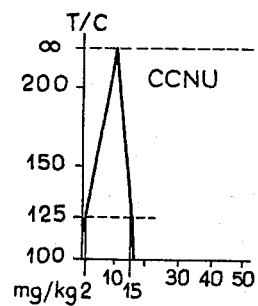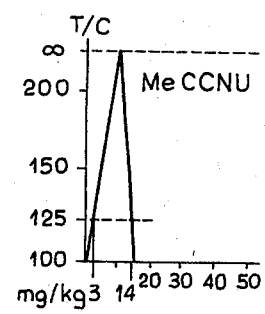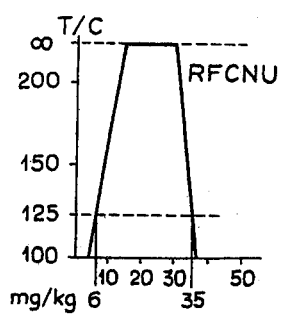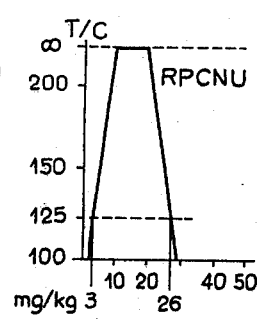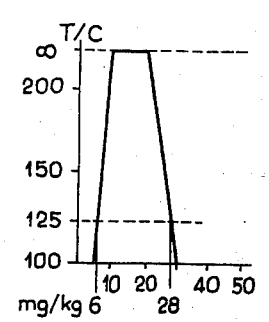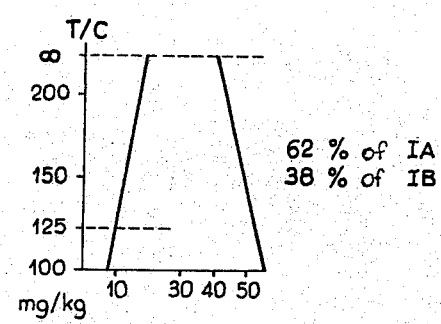

CYSTAMINE DERIVATIVES SUITABLE FOR USE AS MEDICAMENTS

BACKGROUND OF THE INVENTION

The present invention relates to new chemical compounds suitable for use as medicaments and to a process for their preparation.

SUMMARY OF THE INVENTION

More particularly, the present invention relates to compounds of the following general formula:

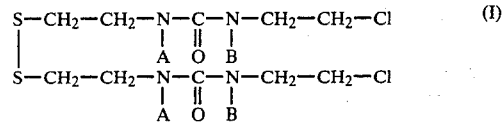

(I)

in which one of the substituents A and B is hydrogen and the other is the radical —N=O.

DETAILED DESCRIPTION

The compounds according to the invention may be prepared by introducing a nitroso group into a compound corresponding to the following formula:

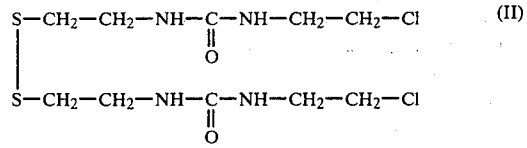

(II)

The introduction of a nitroso group into the compound of formula II may be carried out in particular with nitrosyl chloride or sodium nitrite, particularly using nitrosyl chloride in solution in pyridine, for example at a temperature of from about −5 to about +5° C. and preferably at a temperature of about 0° C., or using sodium nitrite in pure formic acid or in 50% aqueous formic acid. It is also possible to use nitrosyl chloride in dichloromethane, preferably at a temperature below about −10° C.

The compound of formula II may be prepared by condensing cystamine with 2-chloroethyl isocyanate, the cystamine preferably being prepared in situ by reacting triethyl amine with cystamine hydrochloride.

The following plan summarizes the preferred method of synthesis of the compounds according to the present invention.

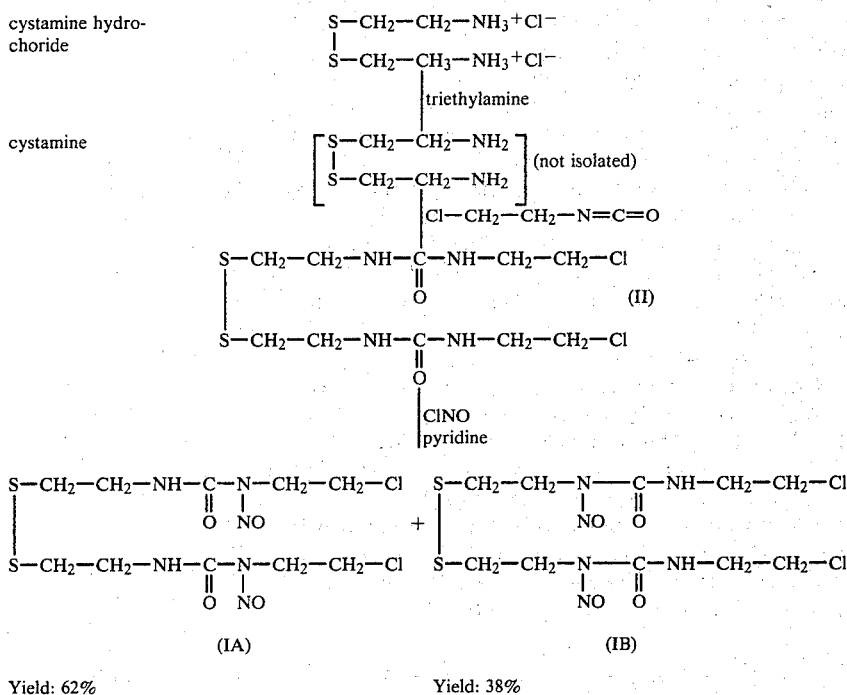

The compounds according to the present invention have proved to be particularly effective in the treatment of certain tumours and particularly in the treatment of leukemia L 1210.

Accordingly, the present invention also relates to the compounds according to the invention as new medicaments and to pharmaceutical compositions containing at least one of the compounds according to the invention as active ingredient.

The pharmaceutical compositions according to the invention are, more particularly, compositions suitable for oral administration, particularly in the form of capsules, because of their low solubility in water.

The daily doses applied may of course vary depending upon the tumour and upon the general state of the patient and, in general, may amount to between 1 and 5 mg/kg per day administered by single injection or by multiple injections.

SPECIFIC EMBODIMENTS

The following Examples are intended to illustrate the preparation of the compounds according to the invention without of course limiting it in any way.

EXAMPLE 1

Preparation of di-[(2-chloroethyl)-2-carbamoyl]-N,N-cystamine (II)

A solution of 50 g (0.22 mole) of cystamine hydrochloride (Fluka) in 200 cc of distilled water was neutralised while stirring at 0° C. with 61 ml (0.44 mole) of freshly distilled triethyl amine (TEA).

After the TEA had been added, 40.3 ml (0.47 mole) of 2-chloroethyl isocyanate (Fluka) were introduced dropwise, the temperature of the reaction mixture being kept at 0° C. The reactant was added over a period of 2 hours, resulting in the deposition of a white powder. At the end of the 2 hour period, the mixture was left overnight with stirring to return to ambient temperature.

The precipitate was centrifuged and washed with $5 \times 100$ cc of iced distilled water, then with $3 \times 100$ cc of a mixture of methanol and ether (60/120) and finally with $2 \times 250$ cc of ether.

After drying in vacuo in a desiccator over phosphoric anhydride, compound II, which crystallised from methanol in the form of colourless platelets, was collected in a yield of 78 g.

M.p.: 144°–145° C.

CCM=Rf: 0.75 (eluent: chloroform-methanol 8-2).

Analysis: $C_{10}H_{20}S_2N_4O_2Cl_2$: calculated (%): C 33.05; H 5.50; N 15.42; observed (%): C 32.96; H 5.96; N 15.26.

IR spectrum $(KBr)\nu cm^{-1}$; (NH)3330; (CH)2960,2920; (C=O)1625; (amide)1570,1520.

NMR spectrum (DMSOd6) NH: (t) centred at 6.28 ppm, 4 H exchangeable for $D_2O$; $CH_2Cl$: (t) centred at 3.56 ppm, 4 H; N—$CH_2$: (m) centred at 3.6 ppm, 8 H; S—$CH_2$: (t) centred at 2.73 ppm, 4 H.

EXAMPLE 2

Preparation of di-[(2-chloroethyl)-2-N-nitroso-N-carbamoyl]-N,N-cystamine (IA)

A stirred suspension of 20 g of compound II (0.055 mole) in 150 cc of anhydrous pyridine was treated at 0° C. by bubbling through nitrosyl chloride. When a homogeneous solution was obtained and when an orange colouration persisted, the evolution of chloride was stopped by continuing stirring at 0° C. for 1 hour.

The solution was then left to return to ambient temperature and thereafter was poured onto 1000 cc of iced distilled water, resulting in the formation of a thick orange-coloured oil.

The mixture was filtered over 150 g of Cellite and washed with distilled water to eliminate the solution from the oil which was retained by the support.

After various washes of the Cellite with ethyl acetate ($4 \times 100$ cc), the organic phases were combined and washed with distilled water ($3 \times 100$ cc). The product was then dried over sodium sulphate and evaporated in vacuo to dryness (temperature of the water bath below 40° C.). An orange-coloured oil which crystallised from ether was collected.

Yield: 96%.

Purification by filtration over 200 g of silica gel (Kieselgel 60=70–230 mesch=Fluka) with ethyl acetate as eluent was necessary. The product was crystallised from a mixture of ethyl acetate and ether (1:9). M.p.: 78°–79° C. CCM=1 spot in 4 systems of different eluents and also 1 spot after several migrations in the two dimensions.

Analysis $C_{10}H_{18}S_2N_6O_4Cl_2$: calculated (%): C 28.50; H 4.27; N 19.95; observed (%): C 28.39; H 4.27; N 20.04.

IR spectrum $(Kbr)\nu cm^{-1}$; (NH)3340; (CH)2960,2940; (C=O)1698; (amide)1530; (N—NO)1480.

NMR spectrum (DMSOd6); NH: (t) centred at 8.92 ppm, 2 H exchangeable for $D_2O$; $CH_2Cl$: (t) centred at 4.02 ppm, 4 H; N—$CH_2$: (m) centred at 3.64 ppm, 8 H; S—$CH_2$: (t) centred at 2.73 ppm, 4 H.

Other signals corresponding to compound IB, di-[(2-chloroethyl)-2-N-carbamoyl]-N,N-nitroso-N,N-cystamine, could be observed in the same spectrum.

The two NH protons were coincident with those of the compound IA and with those of the $CH_2Cl$'s which appeared with the triplet of IA.

The N—$CH_2$ protons which emerged with those of their isomer IA (m), but with a lower intensity, explain the complexity of the signal.

It was only the S—$CH_2$'s which were clearly distinct from the other isomer. They also formed a triplet which was centred at 2.93 ppm instead of 2.73 ppm. By forming the integration ratio between the S—$CH_2$ protons, the two position isomers were present in a proportion of 62% for compound IA and 38% for compound IB.

The uncorrected melting points were measured by capillary using a Gallenkamp apparatus.

The thin-layer chromatographs were prepared on foils of aluminium coated with silica gel (Merck 60F254). The spots were detected with UV light or developed in an iodine atmosphere or by spraying with ninhydrin, followed by heating of the plate. The IR spectra were recorded on a Beckman IR4 spectrograph.

The $^1H$ NMR-spectra were recorded on a Varian HA-100 spectrograph with TMS as the internal reference (d=doublet, t=triplet, m=multiplet).

The compounds according to the present invention were studied on various tumours by comparison with other nitroso ureas also having oncostatic properties:

BCNU
CCNU
MeCCNU
RFCNU
RPCNU and
Chlorozotocine.

These compounds are described in particular in:

J. L. Imbach et al, Biomedicine Express, 1975, 23, 410–13;

J. L. Montero et al, Eur. J. Med. Chem., 1976, 11, 183;

J. L. Montero et al, C.R. Acad. Sc. Paris, Serie C, 1974, t 279, 809;

J. L. Montero et al, Eur. J. Med. Chem. 1978, 13, 421.

The results are shown in the following Table and in the accompanying Figure in which:

T/C (%): average period of survival of the treated mice/average period of survival of the control mice—100.

∞: more than 50% of the treated animals are cured.

It can be seen from this Table and from the accompanying Figure that the products according to the invention have a remarkable oncostatic activity, in particular on L 1210, Lewis Lung Tumour and Colon 26.

In addition, the acute $DL_{50}$ is 70 mg/kg for intraperitoneal administration, i.e. more advantageous than for the other nitroso-ureas mentioned.

TABLE I

| | Effect of 5 nitroso-ureas on various tumours in mice (dose 30 mg/kg administered intraperitoneally) | | | | |
|---|---|---|---|---|---|
| | Compounds | | | | Mixture of 62% of IA 38% of IB |
| Tumours | RFCNU | RPCNU | Chlorozotocine | MeCCNU | |
| L 1210 Intr cerebral | 167 | 114 | 114 | ∞ | ∞ |
| Glioma 26 | 87 | 127 | 127 | 182 | 200 |
| Fibrosarcoma (ICIGC 1) | ∞ | | ∞ | 121 | 118 |
| Lewis Lung Tumour | 100 | 100 | 125 | ∞ | ∞ |
| Colon 26 | 120 | 114 | ∞ | ∞ | ∞ |
| Mammary (TM 2) | 119 | 134 | 105 | 165 | 185 |

We claim:

1. Compounds corresponding to the following formula

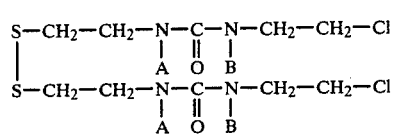 (I)

in which one of the substituents A and B is hydrogen and the other the radical —N=O.

2. Compound according to claim 1 corresponding to the formula

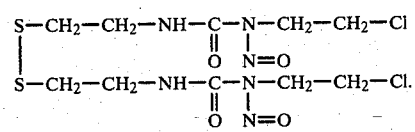

* * * * *